United States Patent [19] [11] 4,219,665
Zeidler et al. [45] Aug. 26, 1980

[54] POLYCARBOXYLIC ACID-2-HYDROXYLALKYL ESTERS, THEIR USE AS EMULSIFYING AGENTS AND COSMETIC EMULSIONS CONTAINING THEM

[75] Inventors: Ulrich Zeidler; Fanny Scheuermann, both of Düsseldorf, Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 920,702

[22] Filed: Jun. 30, 1978

Related U.S. Application Data

[63] Continuation-in-part of Ser. No. 834,460, Sep. 19, 1977, abandoned.

[30] Foreign Application Priority Data

Sep. 20, 1976 [DE] Fed. Rep. of Germany ....... 2642236

[51] Int. Cl.$^2$ ............... C07C 69/34; C07C 69/66; C07C 69/74; C07C 69/78
[52] U.S. Cl. .................... 560/122; 560/89; 560/93; 560/123; 560/127; 560/128; 560/155; 560/169; 560/171; 560/198; 560/182; 560/200
[58] Field of Search ............... 560/89, 93, 122, 127, 560/171, 198, 200, 55, 182, 128, 155, 169

[56] References Cited

U.S. PATENT DOCUMENTS 2,821,542 1/1958 Schmutzler .................... 560/171
3,968,135 7/1976 Steele et al. .................... 560/200

OTHER PUBLICATIONS

Kunishige, Tsutomu et al., "Skin Cosmetic Preparations Containing Cyclopentanetetracarboxylic Acid Esters," Japan, Kokai 74 06,137, (see Chemical Abstracts, vol. 81 (1974), No. 54,328d.).

Primary Examiner—Bernard Helfin
Assistant Examiner—L. Hendriksen
Attorney, Agent, or Firm—Hammond & Littell, Weissenberger and Muserlian

[57] ABSTRACT

Polycarboxylic acid-2-hydroxyalkyl esters of the formula

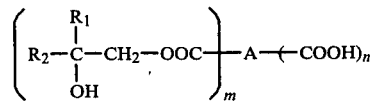

wherein A is an aliphatic, cycloaliphatic, or aromatic radical which is optionally substituted or interrupted by heteroatoms, and/or optionally substituted by hydroxyl groups, $R_1$ is hydrogen or an alkyl radical having 1 to 12 carbon atoms, and $R_2$ is an alkyl radical having 10 to 22 carbon atoms, $n \geq 0$ and $m \geq 2$, with the proviso that $m \geq n$ and the total of $n+m \geq 3$, and their use as emulsifying agents and cosmetic emulsions containing them.

12 Claims, No Drawings

POLYCARBOXYLIC ACID-2-HYDROXYLALKYL ESTERS, THEIR USE AS EMULSIFYING AGENTS AND COSMETIC EMULSIONS CONTAINING THEM

This is a continuation-in-part of copending application Ser. No. 834,460 filed on Sept. 19, 1977, now abandoned.

RELATED ART

In contrast to the production of oil-in-water emulsions, only a limited number of emulsifying agents are available for producing cosmetic emulsions of the water-in-oil type, and moreover, the best of these emulsifying agents are becoming increasingly scarce. Even nowadays, wool fat and its derivatives are still some of the most important bases for emulsifying agents for producing creams of the water-in-oil type. However, despite their uncontested advantages, both wool fat and its derivatives, such as lanolin, have certain disadvantages. Thus conventional water-in-oil emulsifying agents based on wool fat and its derivatives impart a strong characteristic odor to the creams prepared with these substances. This, in turn, requires strong perfuming which frequently cannot be tolerated by persons having sensitive skin. However, this influencing of the quality of the cream by a strong characteristic odor is not only peculiar to wool fat and its derivatives, but also extends to lanolin-free water-in-oil emulsifying agents based on animal sterols, particularly such emulsifying agents based on cholesterol. Furthermore, low-molecular weight emulsifying agents, together with the effective substances of the cream, can be adsorbed by the skin, which is not desirable in all cases.

In addition to the said emulsifying agents based on wool fat, wax alcohols and sterols, the most widely known water-in-oil emulsifier for cosmetic purposes include the oleic acid esters of various polyols, such as glycerin, pentaerythritol, trimethylolpropane and sorbitol. However, due to the unsaturation in their acid component the oleic acid esters have various disadvantages with respect to their technical use, so that there is a genuine need for new and suitable water-in-oil emulsifying agents.

OBJECTS OF THE INVENTION

One object of the present invention is the development of a water-in-oil emulsifying agent which is colorless, odorless, not susceptible to oxidation and which has a spontaneous emulsifying effect.

Another object of the invention is the development of smooth and lustrous cosmetic emulsions or creams which can be satisfactorily distributed on the skin, imparting thereto pleasant and non-sticky feel, and which can in general be used by persons having a sensitive skin.

Another object of the invention is the development of cosmetic emulsions of the above type which are substantially odorless and which, therefore, can find general acceptance when containing only a small and harmless amount of perfume.

A particular object of the invention is the development of an emulsifying agent of the formula

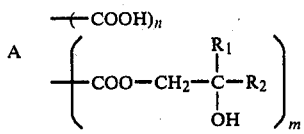

wherein A is an aliphatic, cycloaliphatic, or aromatic radical which is optionally substituted or interrupted by heteroatoms, and/or optionally substituted by hydroxyl groups, $R_1$ is hydrogen or an alkyl radical having 1 to 12 carbon atoms, and $R_2$ is an alkyl radical having 10 to 22 carbon atoms, $n \geq 0$ and $m \geq 2$, with the proviso that $m \geq n$ and the total of $n + m \geq 3$, and of a cosmetic emulsion or cream containing said emulsifying agent.

These and other objects of the present invention will become more apparent as the description thereof proceeds.

DESCRIPTION OF THE INVENTION

It has now been discovered that the above objects have been achieved by the discovery of a polycarboxylic acid-2-hydroxyalkyl ester emulsifying agent of the formula

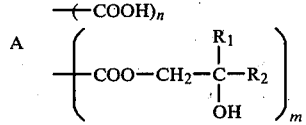

wherein A is a member selected from the group consisting of aliphatic, cycloaliphatic, and aromatic radicals, which is optionally substituted or interrupted by heteratoms, and/or optionally substituted by hydroxyl groups, $R_1$ is a member selected from the group consisting of hydrogen and alkyl radical having 1 to 12 carbon atoms, $R_2$ is an alkyl radical having 10 to 22 carbon atoms, $n \geq 0$ and $m \geq 2$, with the proviso that $m \geq n$ and the total of $n + m \geq 3$.

The present invention provides a cosmetic emulsion or cream of the water-in-oil type containing (1) from 1% to 20% by weight, relative to the total weight of the emulsion, of a polycarboxylic acid-2-hydroxyalkyl ester of the formula

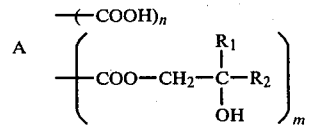

wherein A is a member selected from the group consisting of aliphatic, cycloaliphatic, and aromatic radicals, which is optionally substituted or interrupted by heteroatoms, and/or optionally substituted by hydroxyl groups, $R_1$ is a member selected from the group consisting of hydrogen and alkyl radical having 1 to 12 carbon atoms, $R_2$ is an alkyl radical having 10 to 22 carbon atoms, $n \geq 0$ and $m \geq 2$, with the proviso that $m \geq n$ and the total of $n + m \geq 3$.

(2) from 20% to 75% by weight of water, relative to the total weight of the emulsion, and (3) the remainder to 100% by weight of conventional oily substances used in cosmetic emulsions, such as vegetable and animal fats, waxes, fatty alcohols, hydrocarbons, as well as other auxiliary substances normally used in cosmetic emulsions.

In addition, the present invention provides an improvement in the process of preparing a cosmetic emulsion of the water-in-oil type comprising mixing an emulsifier capable of forming water-in-oil creams with a cosmetically acceptable oily material at elevated temperatures, mixing therewith from 20% to 75% by weight of water, cooling under agitation and recovering said cosmetic emulsion of the water-in-oil type, the improvement consisting of adding (1) from 2% to 20% by weight of the emulsifying agent mentioned above, (2) from 20% to 75% by weight of water and (3) the remainder to 100% by weight of conventional oily substances used in cosmetic emulsions.

The polycarboxylic acid-2-hydroxyalkyl esters of the invention can be produced in a known manner by reacting polycarboxylic acids of the formula

with epoxides of the formula

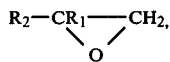

wherein A, $R_1$, $R_2$, n and m are as defined above.

A further method of producing the polycarboxylic acid-2-hydroxyalkyl esters of the invention involves the esterification, by generally known esterification processes, of polycarboxylic acids of the formula

with alkane diols of the formula

wherein A, $R_1$, $R_2$, n and m have the meanings given above.

Basically, all polycarboxylic acids having 3 or more carboxyl groups are suitable as the polycarboxylic acid component of the polycarboxylic acid-2-hydroxyalkyl esters of the invention. Polycarboxylic acids containing 3 to 6 carboxyl groups have been found to be quite effective. The radical A of the polycarboxylic acids can be aliphatic, cycloaliphatic, aromatic, heterocyclic, or combinations of these. A can be straight- or branched-chain, saturated or unsaturated.

Examples of such polycarboxylic acids are tricarballylic acid, β-methyltricarballylic acid, aconitic acid, citric acid, butane-1,2,3,4-tetracarboxylic acid, pentane-1,2,3,4,5-pentacarboxylic acid, hexane-1,2,3,4,5,6,-hexacarboxylic acid, cyclopentane-1,2,3,4,-tetracarboxylic acid, cyclohexane-hexacarboxylic acid, nitrilotriacetic acid, 3,3',3''-nitrilotripropionic acid, ethylenediaminetetraacetic acid, trimellitic acid, trimesic acid, pyromellitic acid, and mellitic acid.

The polycarboxylic acids for use in preparing the esters of the invention are preferably alkane- or alkenepolycarboxylic acids, especially alkane- or alkenepolycarboxylic acids having 3 to 8 carbon atoms in the chain; cycloalkane- or cycloalkenepolycarboxylic acids, especially cycloalkane- or cycloalkenepolycarboxylic acids having 5 to 8, more especially 5 or 6, carbon atoms in the ring; or benzene polycarboxylic acids; as well as hydroxyalkane polycarboxylic acids having 3 to 8 carbon atoms in the alkane chain.

The chains of these polycarboxylic acids can be interrupted by one or more heteroatoms, such as oxygen, sulphur or nitrogen. Those polycarboxylic acids having 1 or 2 such heteroatoms located along the chain, such as nitrilotriacetic acid and ethylenediaminetetraacetic acid, have been found to be particularly useful. The polycarboxylic acids can contain hydroxyl substituents. Polycarboxylic acids having 1 such hydroxyl substituent, such as citric acid, are preferred.

Particularly important polycarboxylic acid components are tricarboxylic acids and tetracarboxylic acids.

The epoxides or diols, used as further starting components of the polycarboxylic acid-2-hydroxyalkyl esters in accordance with the invention, are obtained in a known manner from the corresponding olefins or olefin mixtures. In practice, it has been found advantageous to use mixtures of epoxides or diols of various chain lengths, such as $C_{12-18}$-, $C_{16-18}$-, $C_{16-20}$-, $C_{16-24}$-alkane-1,2-epoxides or alkane-1,2-diols.

Examples of polycarboxylic acid-2-hydroxyalkyl esters of the invention are tricarballylic-tri-2-hydroxy-$C_{12-18}$-alkyl ester and tricarballylic-di-2-hydroxy-$C_{16-18}$-alkyl ester; citric acid-tri-2-hydroxy-$C_{16-20}$-alkyl ester and citric acid-di-2-hydroxy-$C_{16-24}$-alkyl ester; butane-tetracarboxylic acid-tetra-2-hydroxy-$C_{12-18}$-alkyl ester, -tetra-2-hydroxy-$C_{16-18}$-alkyl ester, -tetra-2-hydroxy-$C_{16-20}$-alkyl ester, -tetra-2-hydroxy-$C_{16-24}$-alkyl ester, -tri-2-hydroxy-$C_{12-18}$-alkyl ester, -tri-2-hydroxy-$C_{16-18}$-alkyl ester, -tri-2-hydroxy-$C_{16-20}$-alkyl ester, -di-2-hydroxy-$C_{16-18}$-alkyl ester, and -di-2-hydroxy-$C_{16-20}$-alkyl ester; pentanepentacarboxylic acid-tetra-2-hydroxy-$C_{12-18}$-alkyl ester, -tri-2-hydroxy-$C_{16-18}$-alkyl ester, and -tri-2-hydroxy-$C_{16-20}$-alkyl ester; hexanehexacarboxylic acid-penta-2-hydroxy-$C_{12-18}$-alkyl ester, -tetra-2-hydroxy-$C_{16-18}$-alkyl ester, and -tri-2-hydroxy-$C_{16-20}$-alkyl ester; cyclopentanetetracarboxylic acid-tetra-2-hydroxy-$C_{16-18}$-alkyl ester, -tetra-2-hydroxy-$C_{16-20}$-alkyl ester, -tetra-2-hydroxy-$C_{16-24}$-alkyl ester, -tri-2-hydroxy-$C_{16-18}$-alkyl ester, -tri-2-hydroxy-$C_{16-20}$-alkyl ester, -di-2-hydroxy-$C_{16-18}$-alkyl ester, and -di-2-hydroxy-$C_{16-20}$-alkyl ester; cyclohexanehexacarboxylic acid-hexa-2-hydroxy-$C_{12-18}$-alkyl ester, -tetra-2-hydroxy-$C_{16-18}$-alkyl ester, and -tri-2-hydroxy-$C_{16-20}$-alkyl ester; nitrilotriacetic acid-tri-2-hydroxy-$C_{12-18}$-alkyl ester and -di-2-hydroxy-$C_{16-18}$-alkyl ester; ethylenediaminetetraacetic acid-tetra-2-hydroxy-$C_{16-18}$-alkyl ester, -tri-2-hydroxy-$C_{16-20}$-alkyl ester, and -di-2-hydroxy-$C_{12-18}$-alkyl ester; trimellitic acid-tri-2-hydroxy-$C_{16-18}$-alkyl ester, -tri-2-hydroxy-$C_{16-20}$-alkyl ester, -di-2-hydroxy-$C_{16-18}$-alkyl ester, and -di-2-hydroxy-$C_{16-20}$-alkyl ester; pyromellitic acid-tetra-2-hydroxy-$C_{16-18}$-alkyl ester, -tetra-2-hydroxy-$C_{16-20}$-alkyl ester, and -tri-2-hydroxy-$C_{16-18}$-alkyl ester; trimesic acid-tri-2-hydroxy-$C_{12-18}$-alkyl ester, and -di-2-hydroxy-$C_{16-18}$-alkyl ester; mellitic acid-hexa-2-hydroxy-$C_{16-18}$-alkyl ester, -tetra-2-hydroxy-$C_{12-18}$-alkyl ester, and tri-2-hydroxy-$C_{16-20}$-alkyl ester.

The polycarboxylic acid-2-hydroxyalkyl esters of the invention are eminently suitable as water-in-oil emulsifying agents, particularly for the production of cosmetic emulsions of this type. The special advantages of these emulsifying agents are their spontaneous emulsifying effect and the smooth and lustrous appearance of the creams manufactured therewith. Furthermore, it is to be emphasized that the creams produced therewith can be satisfactorily applied to the skin. The creams are not sticky and impart a pleasant feel to the skin. The emulsifying agents are colorless and odorless and are not susceptible to oxidation. In general, the emulsions produced with the emulsifying agents of the invention can be used by persons having sensitive skin. Since these agents do not have an appreciable intrinsic odor, they do not require heavy perfuming, which in turn has a favorable effect upon compatibility and also saves costs.

Emulsifying agents having particularly good properties are derived from tetracarboxylic acids, particularly from butane-1,2,3,4-tetracarboxylic acid and cyclopentane-1,2,3,4-tetracarboxylic acid. Those compounds having an esterification degree of 3, i.e., three ester moieties in the molecule, are particularly important among these esters derived from tetracarboxylic acids. With respect to the alcoholic ester component, optimum properties are obtained with an average chain length of 16 to 20 carbon atoms. Consequently, preferred polycarboxylic acid-2-hydroxyalkyl esters of the invention are compounds of the general formula

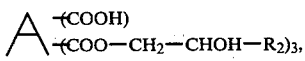

in which A represents an alkane- or cycloalkane residue having 4 to 5 carbon atoms, and $R_2$ represents an alkyl radical having 14 to 18 carbon atoms.

Another important embodiment of the invention are those emulsifying agents derived from citric acid. Examples of particularly important citric acid esters are citric acid-tri-2-hydroxy-$C_{12-14}$-alkyl ester, citric acid-tri-2-hydroxy-$C_{12-18}$-alkyl ester, citric acid-tri-2-hydroxy-$C_{16-18}$-alkyl ester, citric acid-di-2-hydroxy-$C_{12-14}$-alkyl ester, citric acid-di-2-hydroxy-$C_{12-18}$-alkyl ester, and citric acid-di-2-hydroxy-$C_{16-18}$-alkyl ester.

The emulsions in accordance with the invention are produced in a simple and known manner by dissolving the polycarboxylic acid-2-hydroxyalkyl esters, acting as an emulsifying agent, in the oily phase at an elevated temperature of approximately 60° to 70° C. Subsequently, the desired quantity of water, heated to approximately 60° to 65° C., is added, and the emulsion obtained is stirred while cooling.

Cosmetically effective amounts of further constituents of the cosmetic emulsions being manufactured, such as skin moisture regulators, vegetable extracts of effective substances, vitamins, hormones, pigments, salts, perfume oils, UV filtering substances, dyestuffs, etc., are advantageously dissolved or distributed in the phase which absorbs these substances to best advantage. The quantity of emulsifying agent required is 1% to 20% by weight, preferably 2% to 10% by weight, relative to the total cosmetic emulsion. The amount of water to be incorporated can be 20% to 75% by weight, relative to the total cosmetic emulsion.

Products conventionally used, such as animal and vegetable oils and fats, synthetic esters of fatty acids with aliphatic alcohols, higher fatty alcohols, waxes, so-called mineral fats and oils, such as paraffin oil, "Vaseline" ®, ceresine, silicone oils and silicone fats are suitable as the oily phase of the cosmetic emulsions in accordance with the invention.

The invention thus also includes a composition which when agitated with water forms a cosmetic emulsion of the water-in-oil type, comprising (1) from 1% to 20% by weight, relative to the total weight of said composition, of a polycarboxylic acid-2-hydroxyalkyl ester of the formula

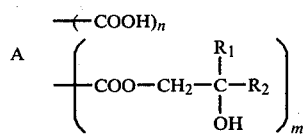

wherein A is a member selected from the group consisting of aliphatic, cycloaliphatic, and aromatic radicals, which is optionally substituted or interrupted by heteroatoms, and/or optionally substituted by hydroxyl groups, $R_1$ is a member selected from the group consisting of hydrogen and an alkyl radical having 1 to 12 carbon atoms, $R_2$ is an alkyl radical having 10 to 22 carbon atoms, $n \geq 0$ and $m \geq 2$, with the proviso that $m \geq n$ and the total of $n + m \geq 3$, and (2) the remainder to 100% by weight of the composition of conventional oily substances used in cosmetic emulsions. Such conventional oily substances include those listed above. In addition, the cosmetic emulsions or creams can contain, if desired, other auxiliary substances normally used in cosmetic emulsions. Examples of such auxiliary substances are skin moisture regulators, vegetable extracts of effective substances, vitamins, hormones, pigments, salts, perfume oils, UV filtering substances, dyestuffs, etc.

The following examples further illustrate the invention, but without limiting the invention to these examples.

EXAMPLES

The production of some of the polycarboxylic acid-2-hydroxy-alkyl esters, to be used in accordance with the invention, will be described in the first instance. In the following examples, 1,2-epoxy-alkanes were used in the preparation of the esters of the invention. The 1,2-epoxy-alkanes employed had the following physical characteristics:

| 1,2-epoxy-alkane | epoxy-value | molecular weight | acid number | iodine number |
|---|---|---|---|---|
| α-$C_{16/18}$-epoxy-alkane ~50% $C_{16}$ ~50% $C_{18}$ | 5.58 | 287 | 1.2 | 2.0 |
| α-$C_{12/18}$-epoxyalkane 30% $C_{12}$ 17% $C_{14}$ 25% $C_{16}$ 25% $C_{18}$ | 6.27 | 255 | 1.4 | 2.2 |
| α-$C_{16/20}$-epoxy-alkane 33⅓% $C_{16}$ 33⅓% $C_{18}$ 33⅓% $C_{20}$ | 5.52 | 290 | 0.9 | 1.9 |
| α-$C_{16/24}$-epoxy-alkane 25% $C_{16}$ 25% $C_{18}$ 25% $C_{20}$ 20% $C_{22}$ 5% $C_{24}$ | 5.09 | 315 | 1.1 | 1.8 |

EXAMPLE 1

Butane-1,2,3,4-tetracarboxylic acid-tri-2-hydroxy-$C_{16-18}$-alkyl ester 234 gm (1 mole) of butane-1,2,3,4-tetracarboxylic acid and 760 gm (3 mole) of $C_{16-18}$-alkane-1,2-epoxide were heated at 120° C. for 4.5 hours under agitation in the presence of 2 percent by weight (20 gm) of benzyldimethylalkyl ammonium chloride. A colorless product having a soft, salve-like quality was obtained after cooling. The characteristic physical data of the compound were as follows: Hydroxyl number=124; saponification number=202; acid number=39.

The polycarboxylic acid-2-hydroxyalkyl esters presented below were obtained in an analogous manner.

EXAMPLE 2

Butane-1,2,3,4-tetracarboxylic acid-tri-2-hydroxy-$C_{12-18}$-alkyl ester

Colorless, salve-like product. Hydroxyl number=128; saponification number=231; acid number=39.

EXAMPLE 3

Butane-1,2,3,4-tetracarboxylic acid-tri-2-hydroxy-$C_{16-20}$-alkyl ester

Colorless, salve-like product. Hydroxyl number=113; saponification number=201; acid number=32.

EXAMPLE 4

Butane-1,2,3,4-tetracarboxylic acid-tetra-2-hydroxy-$C_{12-18}$-alkyl ester

Colorless, salve-like product. Hydroxyl number=156; saponification number=183; acid number=9.

EXAMPLE 5

Butane-1,2,3,4-tetracarboxylic acid-tetra-2-hydroxy-$C_{16-18}$-alkyl ester

Colorless, salve-like product. Hydroxyl number=135; saponification number=172; acid number=9.

EXAMPLE 6

Butane-1,2,3,4-tetracarboxylic acid-tetra-2-hydroxy-$C_{16-20}$-alkyl ester

Colorless, solid product. Hydroxyl number=144; saponification number=159; acid number=8.

EXAMPLE 7

Butane-1,2,3,4-tetracarboxylic acid-tetra-2-hydroxy-$C_{16-24}$-alkyl ester

Colorless, solid product. Hydroxyl number=128; saponification number=151; acid number=7.

EXAMPLE 8

Butane-1,2,3,4-tetracarboxylic acid-di-2-hydroxy-$C_{16-18}$-alkyl ester

Colorless, solid product. Hydroxyl number=114; saponification number=205; acid number=29.

EXAMPLE 9

Butane-1,2,3,4-tetracarboxylic acid-di-2-hydroxy-$C_{16-20}$-alkyl ester

Colorless, solid product. Hydroxyl number=110; saponification number=283; acid number=69.

EXAMPLE 10

Cyclopentane-1,2,3,4-tetracarboxylic acid-tetra-2-hydroxy-$C_{16-18}$-alkyl ester Colorless, salve-like product. Hydroxyl number=131; saponification number=172; acid number=6.

EXAMPLE 11

Cyclopentane-1,2,3,4-tetracarboxylic acid-tetra-2-hydroxy-$C_{16-20}$-alkyl ester Colorless, solid product. Hydroxyl number=125; saponification number=164; acid number=3.

EXAMPLE 12

Cyclopentane-1,2,3,4-tetracarboxylic acid-tetra-2-hydroxy-$C_{16-24}$-alkyl ester Colorless, solid product. Hydroxyl number=117; saponification number=152; acid number=3.

EXAMPLE 13

Cyclopentane-1,2,3,4-tetracarboxylic acid-tri-2-hydroxy-$C_{16-18}$-alkyl ester

Colorless, salve-like product. Hydroxyl number=114; saponification number=202; acid number=29.

EXAMPLE 14

Cyclopentane-1,2,3,4-tetracarboxylic acid-tri-2-hydroxy-$C_{16-20}$-alkyl ester

Colorless, solid product. Hydroxyl number=110; saponification number=198; acid number=29.

EXAMPLE 15

Cyclopentane-1,2,3,4-tetracarboxylic acid-di-2-hydroxy-$C_{16-18}$-alkyl ester

Colorless, solid product. Hydroxyl number=80; saponification number=267; acid number=80.

EXAMPLE 16

Cyclopentane-1,2,3,4-tetracarboxylic acid-di-2-hydroxy-$C_{16-20}$-alkyl ester

Colorless, solid product. Hydroxyl number=76; saponification number=267; acid number=81.

EXAMPLE 17

Pyromellitic acid-tetra-2-hydroxy-$C_{16-18}$-alkyl ester

Colorless, solid product. Hydroxyl number=147; saponification number=158; acid number=26.

EXAMPLE 18

Pyromellitic acid-tetra-2-hydroxy-$C_{16-20}$-alkyl ester

Colorless, solid product. Hydroxyl number=144; saponification number=153; acid number=24.

EXAMPLE 19

Pyromellitic acid-tri-2-hydroxy-$C_{16-18}$-alkyl ester

Colorless, salve-like product. Hydroxyl nunber=122; saponification number=196; acid number=66.

EXAMPLE 20

Trimellitic acid-tri-2-hydroxy-$C_{16-18}$-alkyl ester

Colorless, salve-like product. Hydroxyl number=141; saponification number=162; acid number=9.

EXAMPLE 21

Trimellitic acid-tri-2-hydroxy-$C_{16-20}$-alkyl ester

Colorless, solid product. Hydroxyl number=133; saponification number=159; acid number=12.

EXAMPLE 22

Trimellitic acid-di-2-hydroxy-$C_{16\text{-}20}$-alkyl ester

Colorless, salve-like product. Hydroxyl number = 99; saponification number = 220; acid number = 66.

EXAMPLE 23

Trimellitic acid-di-2-hydroxy-$C_{16\text{-}20}$-alkyl ester

Colorless, solid product. Hydroxyl number = 99; saponification number = 213; acid number = 65.

EXAMPLE 24

Citric acid-tri-2-hydroxy-$C_{12\text{-}14}$-alkyl ester

Colorless, very soft, salve-like product. Hydroxyl number = 205; saponification number = 188; acid number = 10.

EXAMPLE 25

Citric acid-tri-2-hydroxy-$C_{12\text{-}18}$-alkyl ester

Colorless, salve-like product. Hydroxyl number = 172; saponification number = 170; acid number = 9.

EXAMPLE 26

Citric acid-tri-2-hydroxy-$C_{16\text{-}18}$-alkyl ester

Colorless, solid, salve-like product. Hydroxyl number = 150; saponification number = 152; acid number = 10.

EXAMPLE 27

Citric acid-di-2-hydroxy-$C_{12\text{-}14}$-alkyl ester

Colorless, salve-like product. Hydroxyl number = 187; saponification number = 257; acid number = 67.

EXAMPLE 28

Citric acid-di-2-hydroxy-$C_{12\text{-}18}$-alkyl ester

Colorless, salve-like product. Hydroxyl number = 166; saponification number = 237; acid number = 62.

EXAMPLE 29

Citric-acid-di-2-hydroxy-$C_{16\text{-}18}$-alkyl ester

Colorless, solid, salve-like product. Hydroxyl number = 145; saponification number = 218; acid number = 61.

COSMETIC EMULSIONS

The cosmetic water-in-oil skin creams given below were produced by using the above polycarboxylic acid-2-hydroxyalkyl esters as emulsifying agents.

In order to manufacture the creams, the particular emulsifying agent was dissolved in the oily constituents and the oily phase thus obtained was heated to 60° C. Salts, preservatives and other water-soluble constituents were dissolved in the quantity of water required and the aqueous phase obtained was heated to 65° C. The aqueous phase was then slowly introduced into the oily phase under agitation, and the composition was further agitated until it was cold. Stable, smooth, lustrous creams were obtained in all cases. By incorporating further effective substances, such as skin moisture regulators, vegetable extracts, perfume oils, etc., this basic cream can be used to produce skin creams for a wide variety of purposes.

EXAMPLE 30

| Cream based on hardened peanut oil/decyl oleate mixture | |
|---|---|
| Hardened peanut oil | 20 parts by weight |
| Decyl oleate | 20 parts by weight |
| Butane-1,2,3,4-tetracarboxylic acid-tri-2-hydroxy-$C_{16\text{-}18}$-alkyl ester | 4 parts by weight |
| Glyceryl monooleate | 3 parts by weight |
| Beeswax | 3 parts by weight |
| Methyl p-hydroxybenzoate | 0.2 parts by weight |
| Water | 49.8 parts by weight |

EXAMPLE 31

| Cream based on Vaseline$^{(R)}$/paraffin oil/peanut oil mixture | |
|---|---|
| Vaseline$^{(R)}$ | 25 parts by weight |
| Paraffin oil | 20 parts by weight |
| Peanut oil | 5 parts by weight |
| Cyclopentane-1,2,3,4-tetracarboxylic acid-tri-2-hydroxy-$C_{16\text{-}18}$-alkyl ester | 6 parts by weight |
| Methyl p-hydroxybenzoate | 0.2 parts by weight |
| Water | 43.8 parts by weight |

EXAMPLE 32

| Cream based on Vaseline$^{(R)}$/paraffin oil mixture | |
|---|---|
| Vaseline$^{(R)}$ | 8 parts by weight |
| Paraffin oil | 13 parts by weight |
| Isopropyl myristate | 2 parts by weight |
| Butane-1,2,3,4-tetracarboxylic acid-tri-2-hydroxy-$C_{16\text{-}20}$-alkyl ester | 6 parts by weight |
| Glycerol | 4 parts by weight |
| Magnesium sulphate 7 $H_2O$ | 1 parts by weight |
| Zinc oxide | 2 parts by weight |
| Methyl p-hydroxybenzoate | 0.2 parts by weight |
| Water | 63.8 parts by weight |

EXAMPLE 33

| Cream based on Vaseline$^{(R)}$/2-octyldodecanol mixture | |
|---|---|
| Vaseline$^{(R)}$ | 25 parts by weight |
| 2-octyldodecanol | 20 parts by weight |
| Beeswax | 6 parts by weight |
| Cyclopentane-1,2,3,4-tetracarboxylic acid-tri-2-hydroxy-$C_{16\text{-}20}$-alkyl ester | 3.5 parts by weight |
| Aluminum stearate | 1.0 parts by weight |
| Methyl p-hydroxybenzoate | 0.2 parts by weight |
| Water | 44.3 parts by weight |

The other emulsifying agents mentioned above in Examples 1–29 can be used with comparable results in place of the polycarboxylic acid-2-hydroxy-alkyl esters mentioned in Examples 30–33.

The preceding specific embodiments are illustrative of the practice of the invention. It is to be understood, however, that other expedients known to those skilled in the art or disclosed herein, may be employed without departing from the spirit of the invention or the scope of the appended claims.

What we claim is:

1. Polycarboxylic acid-2-hydroxyalkyl esters of the formula

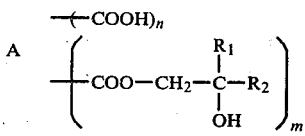

wherein A is a radical derived from polycarboxylic acids having from 3 to 6 carboxyl groups selected from the group consisting of alkane- or alkenepolycarboxylic acids having 3 to 8 carbon atoms in the chain; cycloalkane- or cycloalkenecarboxylic acids having 5 to 8 carbon atoms in the ring; benzene polycarboxylic acids; hydroxyalkane polycarboxylic acids having 3 to 8 carbon atoms in the alkane chain; nitrilotriacetic acid; and ethylenediaminetetraacetic acid, $R_1$ is a member selected from the group consisting of hydrogen and an alkyl radical having 1 to 12 carbon atoms, $R_2$ is an alkyl radical having 10 to 22 carbon atoms, $n \geq 0$ and $m \geq 2$, with the proviso that $m \geq n$ and the total of $n+m \geq 3$.

2. Polycarboxylic acid-2-hydroxyalkyl esters of claim 1, wherein the total of $n+m=4$.

3. Polycarboxylic acid-2-hydroxyalkyl esters of claim 1, wherein $R_2$ is an alkyl radical having 14 to 18 carbon atoms.

4. Polycarboxylic acid-2-hydroxyalkyl esters of claim 1, which are derived from tricarboxylic or tetracarboxylic acids.

5. Polycarboxylic acid-2-hydroxyalkyl esters of claim 1, which are derived from butane-1,2,3,4-tetracarboxylic acid.

6. Polycarboxylic acid-2-hydroxyalkyl esters of claim 1, which are derived from cyclopentane-1,2,3,4-tetracarboxylic acid.

7. Polycarboxylic acid-2-hydroxyalkyl esters of claim 1, which are derived from citric acid.

8. Polycarboxylic acid-2-hydroxyalkyl esters of claim 1, which are derived from citric acid and a 1,2-epoxyalkane selected from the group consisting of
3 mols of 1,2-epoxy-$C_{12-14}$-alkane,
3 mols of 1,2-epoxy-$C_{12-18}$-alkane,
3 mols of 1,2-epoxy-$C_{16-18}$-alkane,
2 mols of 1,2-epoxy-$C_{12-14}$-alkane,
2 mols of 1,2-epoxy-$C_{12-18}$-alkane, and
2 mols of 1,2-epoxy-$C_{16-18}$-alkane.

9. Polycarboxylic acid-2-hydroxyalkyl esters of claim 1, which are derived from mixtures of alkane-1,2-epoxides, wherein the alkane residue has an average chain length within the range from 12 to 24 carbon atoms.

10. Polycarboxylic acid-2-hydroxyalkyl esters of claim 1, wherein A is an alkane residue having from 3 to 8 carbon atoms.

11. Polycarboxylic acid-2-hydroxyalkyl esters of claim 1, wherein A is a cycloalkane residue having from 5 to 6 carbon atoms.

12. Polycarboxylic acid-2-hydroxyalkyl esters of claim 1 of the formula

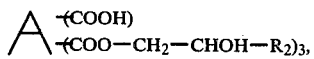

wherein A is a member selected from the group consisting of alkane and cycloalkane residues having 4 or 5 carbon atoms, and $R_2$ is an alkyl radical having 14 to 18 carbon atoms.

* * * * *

UNITED STATES PATENT AND TRADEMARK OFFICE
CERTIFICATE OF CORRECTION

PATENT NO. : 4,219,665
DATED : August 26, 1980
INVENTOR(S) : Ulrich Zeidler, Fanny Scheuermann It is certified that error appears in the above—identified patent and that said Letters Patent is hereby corrected as shown below:

Column 2, lines 35 and 36: "hetera-toms" should read

-- hetero-atoms --.

Signed and Sealed this

Fourteenth Day of July 1981

[SEAL]

Attest:

GERALD J. MOSSINGHOFF

Attesting Officer     *Commissioner of Patents and Trademarks*